United States Patent [19]

Snedeker

[11] Patent Number: 4,926,878
[45] Date of Patent: May 22, 1990

[54] MEDICAL ELECTRODE

[75] Inventor: Marvin L. Snedeker, Grand Rapids, Mich.

[73] Assignee: Labeltape Meditect Inc., Grand Rapids, Mich.

[21] Appl. No.: 291,458

[22] Filed: Dec. 29, 1988

[51] Int. Cl.⁵ .............................................. A61N 1/04
[52] U.S. Cl. ..................................... 128/798; 128/802
[58] Field of Search .............................. 128/639–641, 128/644, 798, 802, 803

[56] References Cited

U.S. PATENT DOCUMENTS

| | | | |
|---|---|---|---|
| 3,817,252 | 6/1974 | Maurer | 128/798 |
| 4,235,241 | 11/1980 | Tabuchi | 128/639 |
| 4,370,984 | 2/1983 | Cartmell | 128/641 X |
| 4,422,461 | 12/1983 | Glumac | 128/798 |
| 4,458,696 | 7/1984 | Larimore | 128/798 |
| 4,580,339 | 4/1986 | Ioffe | 128/641 X |
| 4,643,193 | 2/1987 | DeMarzo | 128/639 |

FOREIGN PATENT DOCUMENTS

86/05083  9/1986  World Int. Prop. O. .......... 128/641

Primary Examiner—Lee S. Cohen
Attorney, Agent, or Firm—Price, Heneveld, Cooper, DeWitt & Litton

[57] ABSTRACT

The specification discloses a medical electrode particularly well suited for use as a tens electrode wherein a conductive stud is coupled to a nonconductive eyelet, the post of which projects through an aperture in a highly conductive dispersive layer, in such a way that the stud base makes direct electrical contact with the dispersive layer. A layer of adhesive coated facestock is adhered to the upper surface of the conductive dispersive layer. The facestock includes an enlarged aperture providing clearance for the stud base. A gel layer is adhered to and overlies the undersurface of the conductive layer.

5 Claims, 2 Drawing Sheets

MEDICAL ELECTRODE

BACKGROUND OF THE INVENTION

The present invention relates to medical electrodes Medical electrodes are adhered to a patient's body to either collect electricity from the body at selected points or to introduce electricity into the body at selected points. Monitoring electrodes and diagnostic electrodes are examples of the former type. So-called "TENS ELECTRODES" are an example of the latter type. The present invention is useful for either type electrode, but is especially adapted for use as a tens electrode.

The typical prior art tens electrode 1 (FIG. 4) includes a layer of facestock 5 adhesively coated on one surface. The facestock is of a nonconductive material and facilitates adhesion of the tens electrode to the patient's body. Adhered to the central portion of the facestock is a highly conductive dispersive layer 2, typically a tin foil layer, which is somewhat smaller in dimensions than the facestock layer. A conductive stud 3 and a conductive eyelet 4 combination function as the electrical contact for the electrode Each includes an upstanding post projecting upwardly from an outwardly radiating base. The eyelet post projects through a small aperture in the dispersive layer and in the facestock layer and into the interior of the stud post. The two are snapped together such that a portion of the dispersive layer and the facestock layer are sandwiched between the respective stud and eyelet bases. The dispersive layer and eyelet base are then covered by a moderately conductive gel layer 6. The gel layer is slightly larger in dimensions than the highly dispersive layer to insure that the dispersive layer does not make direct contact with the patient's body. The function of the highly conductive dispersive layer is to insure that an electrical charge entering through the stud and eyelet connector is dispersed outwardly and evenly across the surface of the gel layer. The gel layer then conducts the dispersed electricity generally evenly into the patient's body.

The gel layer is somewhat smaller in dimensions than the facestock layer so that a portion of the adhesive surface of the facestock layer continues to remain exposed to facilitate adhesion of the entire electrode assembly to the body.

As manufactured, a layer of release liner 7 is provided to cover the entire surface of the facestock and the exposed gel layer. A small "thumb tab" 8 is typically adhered to a portion of the facestock adhesive surface between that surface and the release liner to facilitate peeling the release liner away from the facestock when it is time to use the electrode.

One problem with such a construction when used as a tens electrode is that hot spots tend to be created in the gel layer. There tend to be higher concentrations of electricity directly below the base of the conductive eyelet than in those portions of the gel layer located below the exposed surface of the dispersive layer. It is believed that this results from a tendency for electricity to flow more easily through the silver plated eyelet to the eyelet base than through the conductive dispersive layer.

SUMMARY OF THE INVENTION

In the medical electrode of the present invention, a conductive stud is combined with a nonconductive eyelet and the two are joined through the dispensive layer such that the stud base makes direct contact with the dispersive layer over a substantial portion of the stud base area, rather than with the facestock layer as is the case in conventional medical electrodes. As a result, current flowing into the contact stud flows through the stud base and directly into the dispersive layer. The dispersive layer is the only conductive member contacting the gel layer. The eyelet is nonconductive. As a result, there are no "hot spots" in the gel layer as is encountered in prior art electrodes.

The use of a nonconductive eyelet member is also more economical than the use of a silver plated conductive eyelet. Consequently, the electrode of the present invention may be advantageously used as a monitoring or diagnostic electrode, even though one does not need to worry about "hot spots" in the gel layer of such electrodes.

These and other objects, advantages and features of the invention will be more fully understood and appreciated by reference to the written specification and appended drawings.

DESCRIPTION OF THE PREFERRED EMBODIMENT

Figure 1:
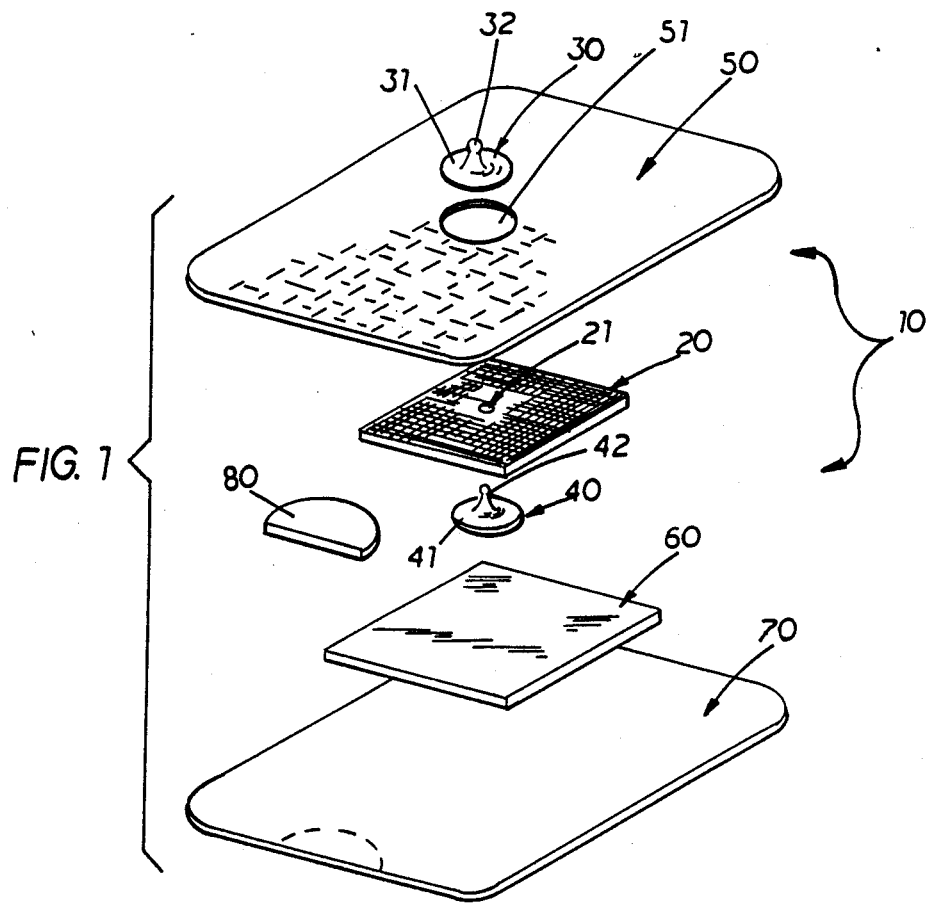
FIG. 1 is a perspective, exploded view showing the components of an electrode made in accordance with the preferred embodiment of the present invention.
Figure 3:
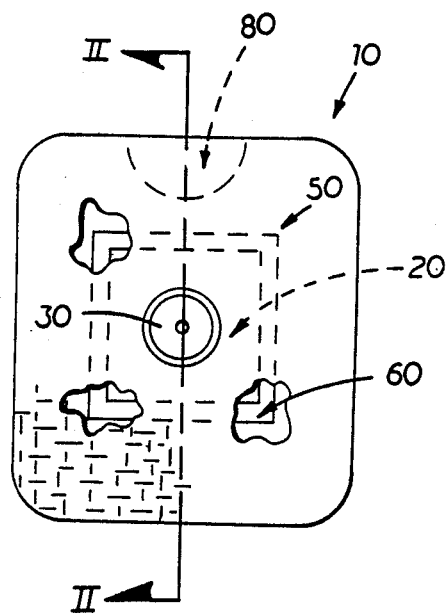
FIG. 3 is a top plan view of the electrode of the preferred embodiment.
Figure 2:
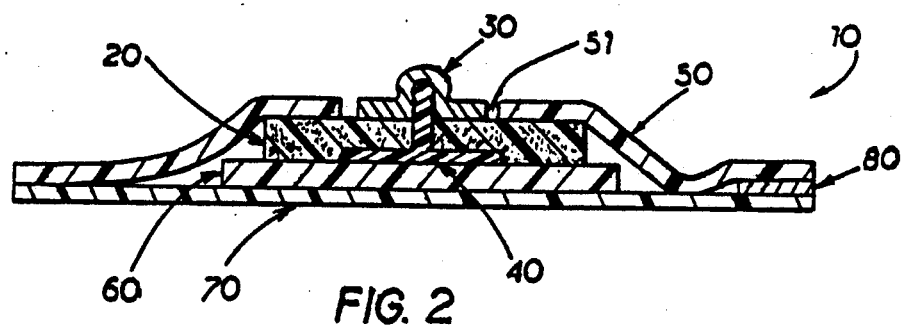
FIG. 2 is a lateral cross-sectional view of the electrode of the preferred embodiment, with the layers being shown somewhat enlarged for purposes of clarity.
Figure 4:
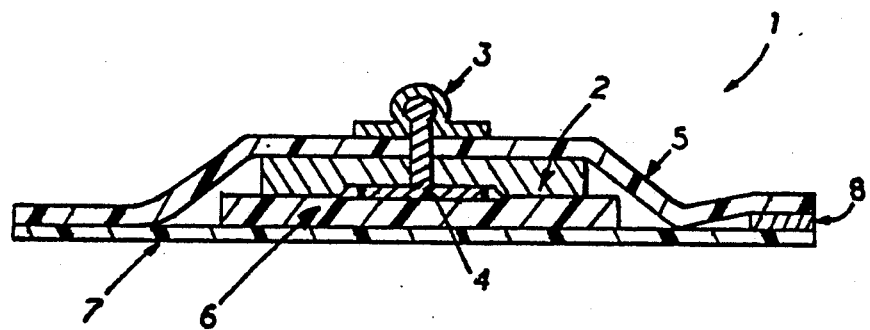
FIG. 4 is a lateral cross-sectional view of a prior art electrode.

In the preferred embodiment, a conductive stud 30 is snapped together with a nonconductive eyelet 40 such that the post 42 of the eyelet projects through an aperture 21 in the dispersive layer 20 and into the receiving interior of the stud post 32 of stud 30 (FIGS. 1 and 2). The stud base 31 of conductive stud 30 makes direct contact with the surface of dispersive layer 20. A layer of facestock 50 includes an adhesive coated undersurface which adheres to the surface of conductive layer 20. An aperture 51 in facestock layer 50 is sufficiently large that it does not interfere with the direct contact between the undersurface of stud base 31 and conductive dispersive layer 20. A layer of dispersive gel 60 completely overlies the bottom surface of conductive dispersive layer 20 and the exposed nonconductive surface of eyelet base 41. A release liner 70 is adhered to exposed adhesive covered portions of facestock 50 so as to cover the entire assembly, there being a small thumb tab 80 adhered to the underside of facestock 50 near an edge thereof to facilitate subsequent peeling of release liner 70 away from the adhesive surface of facestock 50.

Tin or other conductive metal foil is typically used as the conductive dispersive layer 20 in such electrodes and is applicable in the broader aspects of the present invention. However, it is preferable that the material of which conductive layer 20 is made also have sufficient tear strength that the stud 30 and eyelet 40 combination sandwiching conductive layer 20 will not tear out of conductive layer 20 when the electrode is used. To serve this more preferred aspect of the present invention, it is preferable that conductive layer 20 be made of conductive rubber. Other conductive polymeric material having sufficient tear strength could also be used. Such conductive rubber pads have also been used in prior art electrodes and are well-known to those skilled in the art. It is believed that such conductive rubber pads are made by blending a high content of powdered carbon into the rubber blend.

Conductive layer 20 encompasses a sufficient area to comfortably disperse an electric current being introduced into the electrode through stud 30. In the best mode contemplated for the invention, conductive layer 20 is approximately one inch on each side. Conductive layer 20 includes a small aperture 21 in the center thereof through which the post 42 of eyelet 40 can project.

Conductive stud 30 is of a conventional construction, preferably being stainless steel or nickel plated brass to enhance conductivity. It comprises a generally circular stud base 31 from which projects a central stud post 32 which is narrower in diameter than stud base 31.

Eyelet 40 is nonconductive. It is preferably molded of a tough plastic material such as ABS. Such plastic eyelets are commercially available. Eyelet 40 includes a generally circular base 41 from which projects a post 42 which is narrower in diameter than base 41 and which is also slightly narrower in diameter than post 32 of stud 30. The exterior of post 42 and the interior of post 32 are dimensioned such that the two have a snug fit relative to one another when forced together.

Facestock 50 comprises a layer of insulating material such as fabric or foam. In the best mode contemplated, a nonconductive, spun laced polyester fabric material is used. The preferred facestock material is "MED SPUN LACED POLYESTER" TM available from Avery International of Painesville, Ohio. The material is a porous, 2.4 ounce nonwoven material It is coated with an adhesive material, specifically a nonsensitizing acrylic adhesive.

Facestock 50 is larger in dimensions than conductive layer 20 such that a substantial portion of the adhesive on the undersurface of facestock 50 remains exposed after conductive layer 20 is adhered thereto. Facestock layer 50 is, in the best mode contemplated, approximately two and one-half inches by two and one-quarter inches.

Facestock 50 includes a relatively large aperture 51 in the center thereof. Aperture 51 must be sufficiently large that it does not interfere to any substantial degree with intimate electrical contact between the undersurface of base 31 of conductive stud 30 and conductive layer 20. A substantial portion of the surface area of base 31 must make direct, intimate electrical contact with conductive layer 20.

To this end, it is most preferred that aperture 51 be larger in dimensions than the perimeter dimensions of base 31. This greatly facilitates the ease with which firm, intimate electrical contact can be achieved between base 31 and conductive layer 20. It also makes it possible to adhere conductive layer 20 to facestock 50 prior to securing stud 30 and eyelet 40 to conductive layer 20, and still leave base 31 in complete contact over its entire area with conductive layer 20. If such contact were to be achieved where aperture 51 were smaller in diameter than the diameter of base 31, one would have to secure stud 30 and eyelet 40 to conductive layer 20 prior to adhering facestock 50 to conductive layer 20.

Gel layer 60 can be comprised of any conductive gel material. However a preferred material is known in the art as hydrogel. Hydrogel is a polymeric material which is conductive, preferably hydrophylic, has low surface resistivity and good adhesive properties. It is most preferably hypoallergenic and includes a bacteriostat and fungistat. Such materials are well-known to those skilled in the art The best mode of the present invention contemplates the use of MEMTEC TM MN500 available from LecTec Corporation of Minnetonka, Minn.

Hydrogel layer 60 is adhered to and over the undersurface of base 41 of nonconductive eyelet 40 and conductive pad 20. Hydrogel layer 60 is larger in dimension than conductive pad 20 such that no portion of conductive pad 20 makes contact with the patient's skin when electrode 10 is used. Yet, hydrogel layer 60 is still smaller in dimensions than facestock 50 such that a substantial portion of the adhesive undersurface of facestock 50 is still exposed for adhesion to a patient's skin. In a best mode contemplated for the present invention, hydrogel layer 60 is approximately one and one-quarter inch by one and one-half inch.

Release liner 70 is made of any conventional release liner material Examples include silicone coated kraft paper and any plastic material which does not adhere strongly to the acrylic adhesive on the undersurface of facestock 50 In the best mode contemplated for the present invention, a layer of clear polyester plastic material is used as the release liner. Such release liner material is commercially available and is well-known to those skilled in the art.

Release liner 70 is coextensive in dimensions with facestock 50. To facilitate a user peeling release liner 70 away from facestock 50 to expose the adhesive undersurface thereof, a small thumb tab 80, preferably semicircular in configuration, is adhered to the undersurface of facestock 50 along one edge thereof.

To use electrode 10 of the present invention, one separates facestock 50 from release liner 70 in the thumb tab 80 area thereof and subsequently peels release liner 70 away from facestock 50. The electrode is then applied to the patient at the desired location. An electrical coupling or lead is snapped over the post 32 of conductive stud 30 either before or after application of electrode 10 to the patient's body.

Of course, it is understood that the foregoing is merely a preferred embodiment of the invention. Variations on the preferred embodiment would make it possible, for example, to use the invention as a monitoring or diagnostic electrode, rather than as a TENS electrode as described above. Various other changes and alterations can be made without departing from the spirit and broader aspects thereof as set forth in the appended claims, interpreted in accordance with the principles of Patent Law.

The embodiments of the invention in which an exclusive property or privilege is claimed are defined as follows:

1. A medical electrode comprising:
    a highly conductive dispersive layer having an aperture therein and an upper surface and a lower surface;
    a nonconductive eyelet having an eyelet post projecting upwardly from an eyelet base having an upper surface and a lower surface, which base radiates outwardly from said post;
    a conductive stud for mating engagement with said eyelet, said stud including a stud post projecting upwardly from a stud base, said base radiating outwardly from said post;

said post of said eyelet projecting through said aperture in said conductive dispersive layer and matingly engaging the interior of said stud post whereby said stud and eyelet are secured together with said eyelet base contacting said lower surface of said conductive dispersive layer and said stud base making direct electrical contact with said upper surface of said conductive dispersive layer;

a layer of facestock having a adhesive coated undersurface being adhered to the upper surface of said conductive dispersive layer, said facestock having an aperture therein larger in dimensions than said stud base said stud base being entirely within said aperture, and said stud post projecting from said aperture in said facestock whereby the material of said facestock does not interfere with direct electrical contact between said conductive stud base and said conductive dispersive layer;

said facestock being larger in dimensions than said conductive dispersive layer;

a gel layer adhered to and completely covering the lower surface of said eyelet base and the lower surface of said conductive dispersive layer.

2. The electrode of claim 1 in which said gel layer is larger in dimensions than said conductive dispersive layer but smaller in dimensions than said facestock whereby said gel layer is also adhered to a portion of the adhesive coated undersurface of said facestock.

3. The medical electrode of claim 1 in which said dispersive layer comprises a tear resistant material whereby said conductive stud and nonconductive eyelet cannot readily be torn from said dispersive layer.

4. The electrode of claim 3 in which said dispersive layer comprises a conductive polymeric material.

5. The electrode of claim 4 in which said gel layer comprises a layer of hydrogel material.

* * * * *

UNITED STATES PATENT AND TRADEMARK OFFICE
CERTIFICATE OF CORRECTION

PATENT NO. : 4,926,878
DATED : May 22, 1990
INVENTOR(S) : Marvin L. Snedeker

It is certified that error appears in the above-identified patent and that said Letters Patent is hereby corrected as shown below:

Column 1, line 5:
  After "electrodes" (first occurrence) insert --,--

Column 1, line 24:
  After "electrode" insert --,--

Column 3, line 38:
  After "nonwoven material" insert --,--

Column 4, line 8:
  After "art" insert --,--

Column 4, line 24:
  After "material" insert --,--

Column 4, line 27:
  After "50" insert --,--

Column 5, claim 1, line 11:
  "a adhesive" should be --an adhesive--

Signed and Sealed this

Twenty-first Day of January, 1992

*Attest:*

HARRY F. MANBECK, JR.

*Attesting Officer*   *Commissioner of Patents and Trademarks*